United States Patent [19]
Mitchell

[11] Patent Number: 5,809,185
[45] Date of Patent: Sep. 15, 1998

[54] SENSOR FOR DETECTING MICROORGANISMS

[76] Inventor: Ralph Mitchell, 27 Mason St., Lexington, Mass. 02173

[21] Appl. No.: 638,278

[22] Filed: Apr. 26, 1996

[51] Int. Cl.$^6$ .................................................... G02B 6/26
[52] U.S. Cl. ........................ 385/12; 385/128; 250/227.11
[58] Field of Search ............... 385/12, 128; 250/227.11, 250/227.14, 227.18

[56] References Cited

U.S. PATENT DOCUMENTS 5,496,700  3/1996  Ligler et al. ............... 435/7.1

OTHER PUBLICATIONS

Flemimger et al; Applied and Enviromental Microbiology, Dec. 1995, pp. 4357–4361.
Brecht et al; "Optical Probes and Transducers"; Biosensors & Bioelectronics; pp. 923–936, 1995.

*Primary Examiner*—John Ngo
*Attorney, Agent, or Firm*—Iandiorio & Teska

[57] ABSTRACT

A sensor for detecting microorganisms in air, water, or deposited on surfaces. The sensor includes a source of light, a waveguide receptive to the source of light, a fluorochrome coating on the waveguide, and a detector which detects the Stokes shift of light passing through the waveguide in response to microorganisms fluorescing as they come into contact with the fluorochrome coating on the waveguide.

12 Claims, 3 Drawing Sheets

SENSOR FOR DETECTING MICROORGANISMS

FIELD OF INVENTION

This invention relates to a sensor for detecting microbial biofilms, biological weapons, and harmful microorganisms in air and water as well as beneficial or harmful microorganisms depositing on surfaces.

BACKGROUND OF INVENTION

Biofilms, formed of a layer of bacteria or fungi, are generally undesirable. They contaminate heat exchangers, respirators, condensers, drinking water, indoor air vents and other devices. For example, the electrical utility industry regularly uses environmentally unsafe chlorine to remove biofilm build-up in condensers. In other applications, however, certain bacteria, fungi, and biofilms are desirable. For example, certain bacteria are often used in the treatment of hazardous waste material and in other bioreactors.

Techniques currently used to detect the presence of a bio-film, however, involve the use of cumbersome equipment. For example, the currently available cytometers and spectrofluorimeters used for measuring and counting organic cells cannot be used in situ, and the actual detection and analysis of biofilms takes a significant amount of laboratory time.

In many cases, there is a need for very rapid detection of biological substances being deposited on surfaces. One such application is the detection of biological weapons in order to prevent harm or loss of life to military personnel or civilians. By the time a cytometer is used and the related technical analysis performed, a biological weapon may already have caused severe and irreparable harm. In medical equipment such as respirators, it is desirable to detect the formation of biofilms in situ before a patient is infected with potentially harmful human pathogenic microorganisms.

SUMMARY OF INVENTION

It is therefore an object of this invention to provide a sensor for detecting microorganisms which provides a very rapid response time.

It is a further object of this invention to provide such a sensor which is small and lightweight.

It is a further object of this invention to provide such a sensor which is fully self-contained and portable.

It is a further object of this invention to provide such a sensor which can be used in situ.

It is a further object of this invention to provide such a sensor which requires minimal maintenance and is highly reliable.

It is a further object of this invention to provide such a sensor which has the ability to detect a wide variety of microorganisms.

This invention results from the realization that microorganisms indicative of biofilms or the use of biological weapons can be quickly detected in a small, lightweight, portable, and self-contained sensor which detects the Stokes shift of light traveling through a fluorochrome coated waveguide in response to microorganisms fluorescing as they come into contact with the fluorochrome coating.

This invention features a sensor for detecting microorganisms in air, water, or deposited on surfaces. The sensor comprises a source of light; a waveguide receptive to the source of light; a fluorochrome coating on the waveguide; and means for detecting the Stokes shift of the light passing through the waveguide in response to microorganisms fluorescing as they come into contact with the fluorochrome coating. The waveguide is preferably a porous optical fiber and the source of light is broadband such as a tungsten lamp. Alternatively, the source of light includes a source of coherent light. There may be a filter disposed between the source of light and the waveguide and another filter disposed between the waveguide and the detector. The filters are chosen based on the particular fluorochrome coating used.

The means for detecting preferably includes a photodetector tuned to detect the Stokes shift and there is also an indicator for providing an indication of the presence of a detected microorganism.

In a preferred embodiment, there is at least one source of light; a plurality of waveguides receptive to the source of light; a different fluorochrome coating on each waveguide; and means for separately detecting the Stokes shift of the light traveling through the waveguides in response to different microorganisms fluorescing as they come into contact with the different fluorochrome coatings on the waveguides.

DISCLOSURE OF PREFERRED EMBODIMENT

Other objects, features and advantages will occur to those skilled in the art from the following description of a preferred embodiment and the accompanying drawings, in which.

Figure 1:
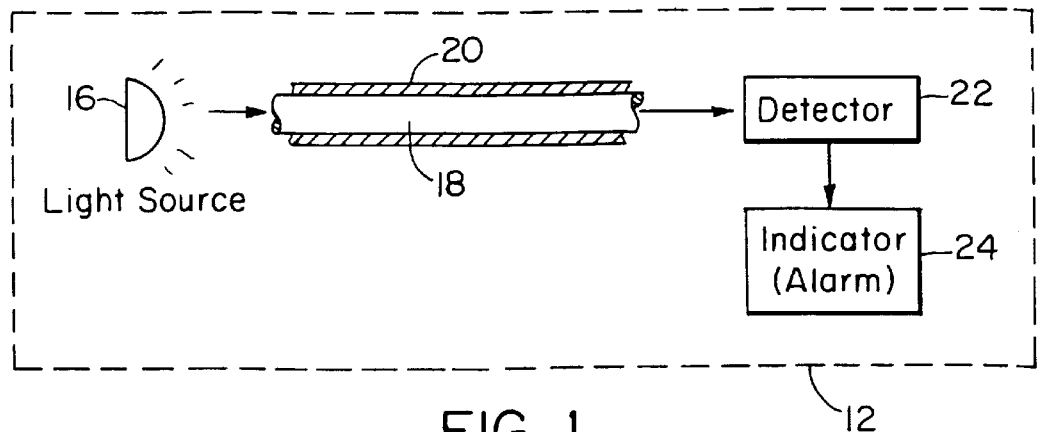
FIG. 1 is a block diagram of the sensor for detecting microorganisms according to this invention.

Sensor 12, FIG. 1, includes light source 16, which may be a broadband source of light (e.g., a tungsten lamp), or a coherent source of light such as a laser. Waveguide 18 is receptive to light source 16 as shown and includes a fluorochrome coating 20 thereon.

As microorganisms come into contact with fluorochrome coating 20, a Stokes shift occurs in the light traveling within waveguide 18. Different types of fluorochrome compounds are used to detect different types of microorganisms as explained in *Flow Cytometry* by Alice Longobardi Givan (1993), pp. 60–107, incorporated herein by this reference. Waveguide 18 is preferably a porous glass optical fiber available from Radiant Communication Corp. of N.J., but other types of waveguides may be used. Fluorochrome coating 20 may be effected by dipping optical fiber 18 in the fluorochrome composition and allowing it to dry.

Figure 2:
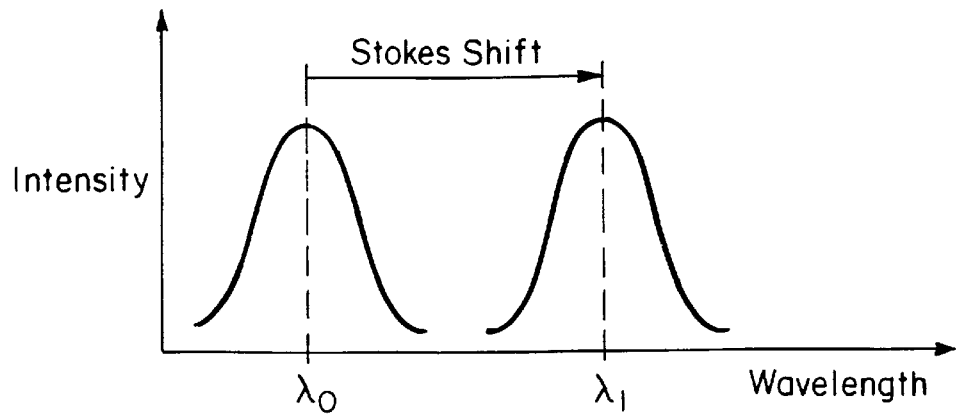
FIG. 2 is a graph showing the detection of the Stokes wavelength shift in accordance with the sensor shown in FIG. 1.
Figure 4:
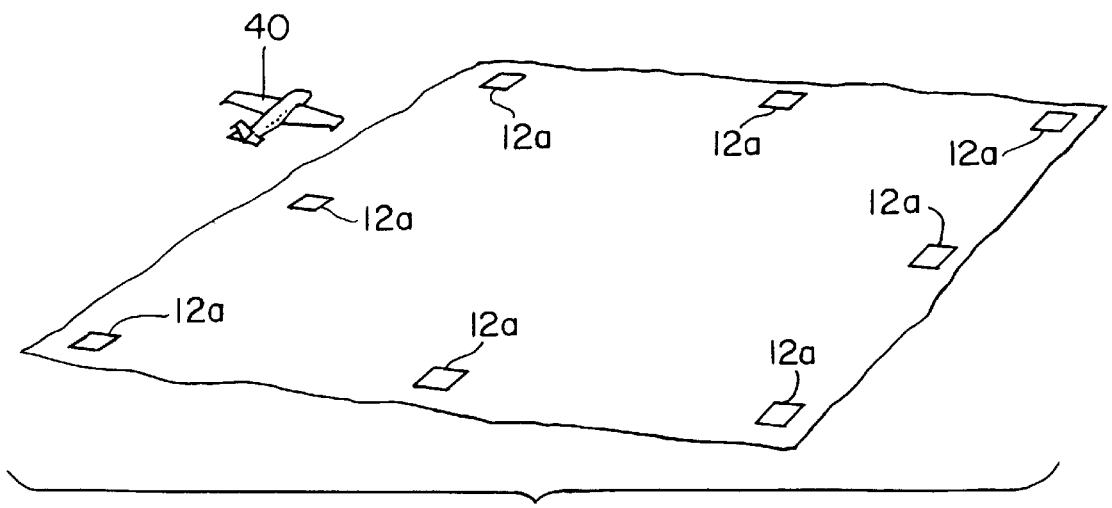
FIG. 4 is a schematic view showing one implementation of the sensor shown in FIG. 3 for detecting the use of biological weapons.

As shown in FIG. 2, optical fiber 18, coated with a particular fluorochrome composition 20, presents a wavelength $\lambda_0$ to detector 22, FIG. 1. In the presence of a microorganism which fluoresces in the presence of fluorochrome composition 20, however, the wavelength of the light received at detector 22 will be shifted to $\lambda_{-1}$ as shown. Detector 42 is a photocell or photomultiplier device tuned to only detect wavelengths proximate $\lambda_{-1}$, and then, in response, provides a signal to indicator 24 which includes a visible and/or audible alarm. The shift from $\lambda_0$ to $\lambda_{-1}$ is known as the Stokes shift, explained in *Flow Cytometry*, supra.

Figure 3:
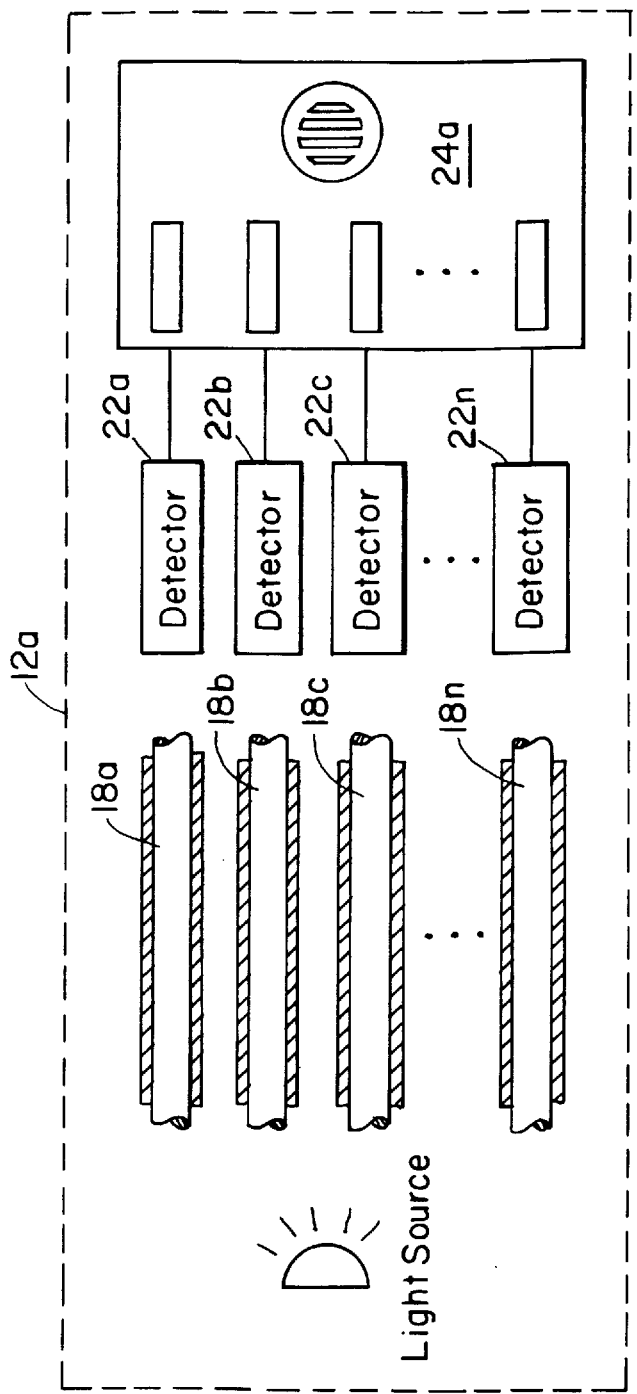
FIG. 3 is a block diagram of another embodiment of the sensor for detecting microorganisms in accordance with this invention wherein the sensor has the ability separately to detect a number of different microorganisms.
Figure 5:
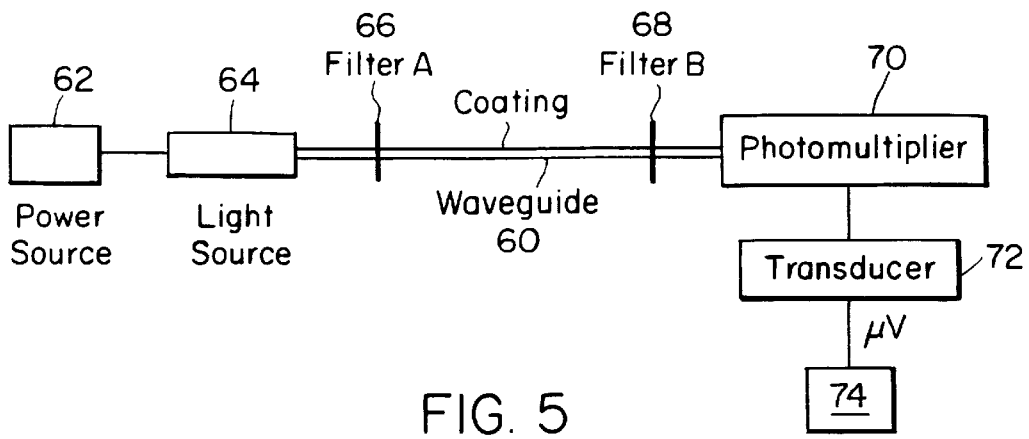
FIG. 5 is a block diagram of a laboratory sensor used to prove the concept of the present invention.
Figure 6:
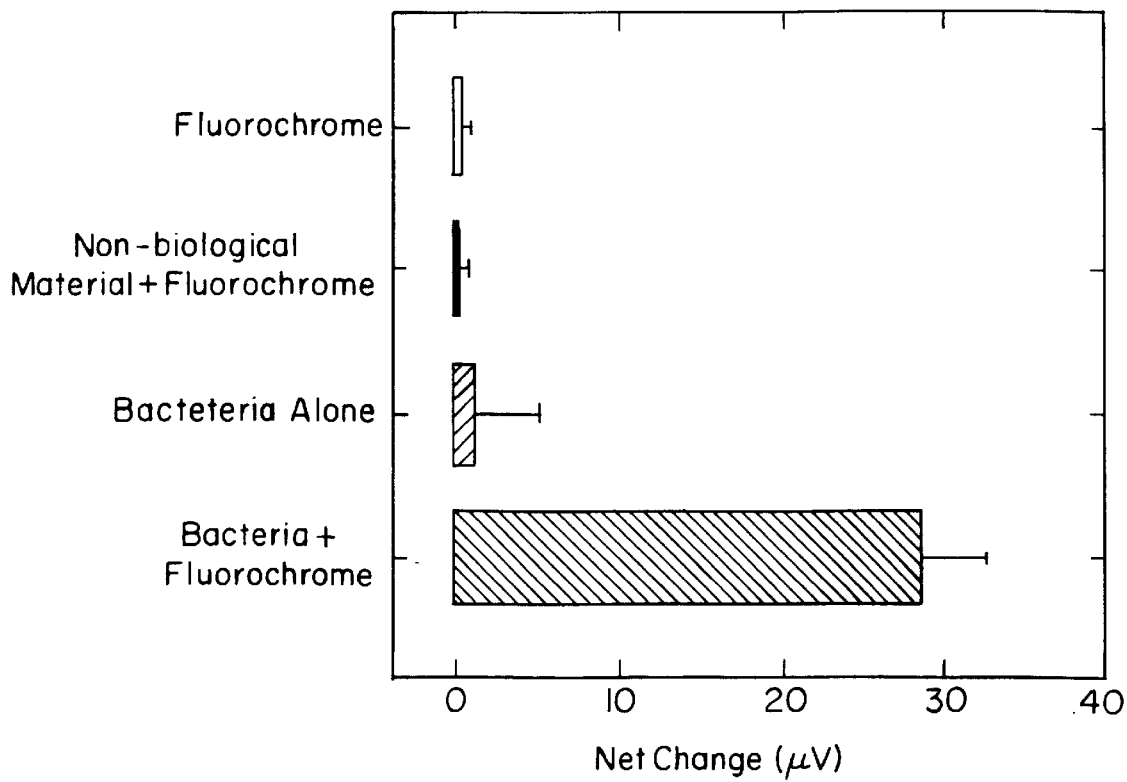
FIG. 6 is a graph showing the effect of the Stokes wavelength shift which occurred in the laboratory sensor shown in FIG. 5.

A number of particular fluorochrome compositions have been formulated and each type is usually particularly suited to the detection of certain types of microorganisms. Table I shows a number of different types of fluorochromes which may be used as fluorochrome coating 20, FIG. 1, as well as other fluorochromes described in the book *Flow Cytometry*, supra, Table 5.1, page 65, incorporated herein by this reference.

can be made small and lightweight. Sensors 12, FIG. 1 and 12a, FIG. 3, are fully self-contained and portable and therefore can be used in situ. Such a sensor requires minimal maintenance and is highly reliable. By using different fluorochrome compositions, sensor 12*a*, FIG. 4, has the ability to detect a wide variety of microorganisms.

In the laboratory, a porous glass optical fiber 60, FIG. 5, was dipped in a gelatinous solution of acridine orange or DAPI and allowed to dry. Power via power source 62 was used to energize light source 64, a 15-watt (500–1000 $\mu$V) Halogen lamp. 425 nm filter 66 was placed between light source 64 and optical fiber 60 and filter 68 which only passes wavelengths greater than 650 nm was placed between optical fiber 60 and photomultiplier 70 (a diode light meter).

TABLE I

| FLUOROCHROME | CHEMICAL FORMULA | | ABS. | EMIS. | USE |
|---|---|---|---|---|---|
| CTC | 5-cyano-2,3-ditolyl tetrazolium chloride | | 450–490 nm | 620 nm | Vital redox stain |
| DAPI | 4,6-diamino-2-phenylindole | | 365 nm | 475 nm | Nucleic acids (live cells) |
| Ehtidium Bromide | $C_{21}H_{20}N_3Br$ | | 517 nm | 625 nm | Stains DNA of dead cells |
| Acridine Orange | $C_{17}H_{20}N_3Cl$ | DNA: | 480 nm | 510 nm | Nucleic acids (live cells) |
| | | RNA: | 440–470 nm | 650 nm | |
| FITC | Fluorosecein isothiocyanate | | 480 nm | 525 nm | Detection of antigen/antibody Rx's |
| Calcein AM | (Propr. Molecular Probes) | | | 475 nm | Vital redox stain |
| Rhodamine 101 | $C_{28}H_{31}ClN_2O_3$ | | 590 nm | 625 nm | Detection of antigen/antibody Rx's flow cytometry |
| Acriflavin | $C_{14}H_{15}N_3Cl_2$ | | Violet | Green | Nucleic acids, may be biocidal |
| Propidium Iodide | | | 493 nm | 630 nm | DNA only |
| Calcofluor White | $C_{44}H_{34}N_{12}O_6S_2Na_2$ | | U.V. | Blue-green | Fungal cell walls |
| Aniline Blue | $C_{32}H_{25}N_3O_9S_3Na_2$ | | 377 nm | 520 nm | Specific to 1–3 B-D-glucans in fungi |

So, for example, if the biological weapon "anthrax" is to be detected, fluorochrome coating 20, FIG. 1, may be DAPI or Acridine Orange. A coating of Ethidium Bromide may be used to detect when the "anthrax" microorganisms are rendered non-viable. A DAPI coating may also be used to detect the presence of a biofilm in a heat exchanger or other device and Calcofluor White may be used to detect fungi thereby providing a rapid indication of the quality of the air within a room, building, or other space. Waveguide 18 is preferably a porous optical fiber so that the fluorochrome coating permeates at least partially into the surface of the optical fiber.

Sensor 12 is particularly efficient and reliable since dust does not affect transmission of light from light source 16 through waveguide 18, thereby eliminating false positive readings. Used as a part of the chemical weapon detection system, sensor 12*a*, FIG. 3, includes a number of waveguides 18*a*, 18*b*, 18*c*, . . . 18*n*, each coated with a different fluorochrome coating. Detectors 22*a*, 22*b*, 22*c* . . . 22*n*, are each tuned in accordance with the particular fluorochrome coating used and the microorganism to be detected to provide a signal to indicator 24*a* which provides a visible or and/or audible indication of the type of biological weapon detected. Such a sensor 12*a* may be made extremely small and lightweight and self-contained with its own power supply. Portable units may be placed on airplane or drone 40, FIG. 4, and in situ units may be placed as shown around the perimeter of a military installation or battlefield.

Such a sensor, unlike currently used cytometers and spectrofluorimeters, provide a very rapid response time and Transducer 72, a microvolt amplifier from Kethley Instruments in Ohio, connected to the photomultiplier 70 then outputs a voltage to voltmeter 74.

As shown in FIG. 6, the presence of the acridine orange or DAPI coating alone on the porous glass waveguide resulted in a small net voltage change detected by voltmeter 74, FIG. 5. The same is true when non-biological material (i.e., dust particles) came into contact with the fluorochrome coating or when bacteria of the genus pseudomonas came into contact with an optical fiber without the fluorochrome coating as shown.

When the same bacteria came into contact with the fluorochrome coated optical fiber, however, a change in voltage on the order of 25 $\mu$V was detected by voltmeter 74, FIG. 5, indicating the presence of the Stokes shift discussed with reference to FIG. 2.

The choice of filter 66, FIG. 5, and filter 68 will depend on the actual fluorochrome coating used (see Table 1). Filter 66 should pass light in the range of wavelengths that the particular fluorochrome coating absorbs light and filter 68 should pass light in the range of wavelengths that the particular fluorochrome coating emits light when subjected to the bacteria to be detected.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A sensor for detecting microorganisms, the sensor comprising:
    a source of light;
    a waveguide receptive to said source of light;
    a fluorochrome coating on the waveguide; and
    means for detecting the Stokes shift of the light passing through the waveguide in response to microorganisms fluorescing as they come into contact with the fluorochrome coating.

2. The sensor of claim 1 in which said waveguide is a porous optical fiber.

3. The sensor of claim 1 in which said source of light is broadband.

4. The sensor of claim 3 in which said broadband source of light includes a tungsten lamp.

5. The sensor of claim 1 in which said source of light includes a source of coherent light.

6. The sensor of claim 1 in which said means for detecting includes a photodetector tuned to detect said Stokes shift.

7. The sensor of claim 1 further including an indicator, responsive to said means for detecting, for providing an indication of the presence of a detected microorganism.

8. The sensor of claim 1 further including a first filter disposed between the source of light and the waveguide and a second filter disposed between the waveguide and the means for detecting.

9. The sensor of claim 8 in which the first filter passes light in wavelengths corresponding to the absorbance of the fluorochrome coating and the second filter passes light in wavelengths corresponding to the emissivity of the fluorochrome coating.

10. A sensor for detecting microorganisms, the sensor comprising:
    at least one source of light;
    a plurality of waveguides receptive to said source of light;
    a different fluorochrome coating on each said waveguide; and
    means for separately detecting the Stokes shift of the light traveling through the waveguides in response to different microorganisms fluorescing as they come into contact with the different fluorochrome coatings on the waveguides.

11. A sensor for detecting microorganisms, the sensor comprising:
    a source of light;
    a waveguide receptive to said source of light;
    a first filter disposed between the source of light and the waveguide;
    a fluorochrome coating on the waveguide;
    means for detecting the Stokes shift of the light passing through the waveguide in response to microorganisms fluorescing as they come into contact with the fluorochrome coating; and
    a second filter disposed between the waveguide and the means for detecting.

12. The sensor of claim 11 in which the first filter passes light in wavelengths corresponding to the absorbance of the fluorochrome coating and the second filter passes light in wavelengths corresponding to the emissivity of the fluorochrome coating.

* * * * *